US011847187B2

(12) United States Patent
Noguchi et al.

(10) Patent No.: US 11,847,187 B2
(45) Date of Patent: Dec. 19, 2023

(54) DEVICE IDENTIFICATION DEVICE, DEVICE IDENTIFICATION METHOD, AND DEVICE IDENTIFICATION PROGRAM

(71) Applicant: Nippon Telegraph and Telephone Corporation, Tokyo (JP)

(72) Inventors: Hirofumi Noguchi, Musashino (JP); Misao Kataoka, Musashino (JP); Takuma Isoda, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 127 days.

(21) Appl. No.: 17/636,485

(22) PCT Filed: Aug. 23, 2019

(86) PCT No.: PCT/JP2019/033116
§ 371 (c)(1),
(2) Date: Feb. 18, 2022

(87) PCT Pub. No.: WO2021/038639
PCT Pub. Date: Mar. 4, 2021

(65) Prior Publication Data
US 2022/0276954 A1 Sep. 1, 2022

(51) Int. Cl.
*G06F 18/00* (2023.01)
*G06F 18/22* (2023.01)
(Continued)

(52) U.S. Cl.
CPC .......... *G06F 18/22* (2023.01); *G06F 11/3688* (2013.01); *G06F 11/3692* (2013.01);
(Continued)

(58) Field of Classification Search
CPC .... G06F 21/55; G06F 21/6254; G06F 18/214; G06F 18/22; G16H 50/70; G06N 20/00
See application file for complete search history.

(56) References Cited

U.S. PATENT DOCUMENTS

2002/0161763 A1* 10/2002 Ye ........................ G06F 21/55
2017/0039487 A1* 2/2017 Naganuma .......... G06F 21/6254
2017/0255669 A1* 9/2017 Ronen .................... G16H 50/70

OTHER PUBLICATIONS

Cao et al, CN 108564136, (translation), May 3, 2019,15 pgs <CN_108564136.pdf>.*
(Continued)

*Primary Examiner* — Tuan A Vu
(74) *Attorney, Agent, or Firm* — Fish & Richardson P.C.

(57) ABSTRACT

A device identification apparatus includes: a communication information collection unit configured to acquire communication information of existing devices and an identification target device; a feature amount generation unit configured to make the communication information of the existing devices' feature amounts and assign labels to generate first training data, make the communication information of the identification target device feature amounts and assign a dummy label to generate second training data, and further acquire communication information of the identification target device to generate identification data; a machine learning unit configured to cause a learning engine to learn the training data, and input the identification data to classify the identification data into the labels; a degree-of-similarity calculation unit configured to calculate a degree of similarity for each label; and a device identification unit configured to use a new type determination threshold to determine whether the device is a new type device.

9 Claims, 12 Drawing Sheets

(51) Int. Cl.
  *G06N 20/00* (2019.01)
  *G06F 11/36* (2006.01)
  *G06F 18/214* (2023.01)
  *G06F 18/21* (2023.01)
  *G06F 21/55* (2013.01)
  *G06F 21/62* (2013.01)
  *G16H 50/70* (2018.01)

(52) U.S. Cl.
  CPC .......... *G06F 18/214* (2023.01); *G06F 18/217* (2023.01); *G06N 20/00* (2019.01); *G06F 21/55* (2013.01); *G06F 21/6254* (2013.01); *G16H 50/70* (2018.01)

(56) References Cited

OTHER PUBLICATIONS

Ma et al, CN 109948708, (translation), Jun. 28, 2019, 11 pgs < CN_109948708.pdf>.*
Noguchi et al., "Device Identification Based on Communication Analysis for the Internet of Things," IEEE Access, 2019, 7:52903-52912.

* cited by examiner

Fig. 3

| LABEL | LABEL "MODEL A" | LABEL "MODEL B" | LABEL "MODEL C" | ... | DUMMY LABEL |
|---|---|---|---|---|---|
| NUMBER OF PIECES OF CLASSIFIED FEATURE AMOUNT DATA | FEATURE AMOUNT (IDENTIFICATION TARGET)<br>1 | 0 | FEATURE AMOUNT (IDENTIFICATION TARGET)<br>5 | ... | FEATURE AMOUNT (IDENTIFICATION TARGET)<br>6 |
| DEGREE OF SIMILARITY | 1/6 * 100<br>=17% | 0/6 * 100<br>=0% | 5/6 * 100<br>=83% | ... | |

DEVICE IDENTIFICATION DEVICE, DEVICE IDENTIFICATION METHOD, AND DEVICE IDENTIFICATION PROGRAM

CROSS-REFERENCE TO RELATED APPLICATIONS

This application is a National Stage application under 35 U.S.C. § 371 of International Application No. PCT/JP2019/033116, having an International Filing Date of Aug. 23, 2019. The disclosure of the prior application is considered part of the disclosure of this application, and is incorporated in its entirety into this application.

TECHNICAL FIELD

The present invention relates to a device identification apparatus, a device identification method, and a device identification program that identify a device connected to a network.

BACKGROUND ART

Today, the Internet of Things (IoT) continues to expand rapidly, and a wide variety and a large number of devices are being connected to a network. There is a forecast that 50 billion devices are connected to the Internet in 2020, and more and more devices are expected to be installed in a variety of environments such as homes, factory, and streets. Moreover, there are various types of devices connected to a network, including sensors such as a camera or a thermometer, small computers such as a smartphone, actuators such as a speaker or a display, and the like, and computational processing capabilities and protocols vary widely. An administrator of devices in each environment is required to accurately grasp and manage a nature and a state of each device so as to properly and safely use a wide variety and an enormous number of devices described above.

Examples of information that is influential in managing IoT devices include a "class" and a "model" of a device. Here, the class of a device refers to a rough classification corresponding to a function such as a camera, a speaker, a printer, a smartphone, a personal computer, or the like. The model is information capable of specifically identifying a product, which can be expressed as model number xx available from A Corporation, for example. For a device connected to a network, when an administrator can grasp these pieces of information, it has a great advantage for asset management of devices or service utilization. Accordingly, it is required that only connection to the network can automatically display these pieces of information for the administrator.

For a device connected to a network, there is disclosed a technique of using communication information to identify a device (see NPL 1). A technology described in NPL 1 extracts a feature amount from communication information transmitted and received by a device in a network, and calculates a degree of similarity with accumulated data collected by a similar procedure in the past to finally identify an identical device. The accumulated data is obtained by collecting an average of or an increase and decrease trend in a traffic amount within a certain period of time, and the like in types or models of devices, and is assumed to be collected before performing device identification processing, i.e., in advance. In the technology described in NPL 1, for a device having the highest degree of similarity among degrees of similarity obtained from a feature amount of communication information of an identification target device and accumulated data of devices, when the degree of similarity is less than a certain threshold (new type determination threshold), the device is determined to be a new type device for which there is no data accumulated in advance.

CITATION LIST

Non Patent Literature

NPL 1: HIROFUMI NOGUCHI, MISAO KATAOKA, and YOJI YAMATO; "Device Identification Based on Communication Analysis for the Internet of Things," IEEE Access, Volume 7, 2019, P. 52903-52912

SUMMARY OF THE INVENTION

Technical Problem

In order to apply machine learning to and automate the determination technique of the new type device, which is the technology described in NPL 1 described above, there are two problems to be improved, as described below. Note that the present invention aims to perform more accurate classification than that of the related art by applying machine learning to determination of a new type device.

A first problem is a problem brought to the fore when machine learning is applied to calculation of a degree of similarity between an identification target and accumulated data. In the technology described in NPL 1, it is assumed that a degree of similarity is expressed in an absolute amount, and, for example, when feature amounts of a device A, a device B, and a device C are previously collected as accumulated data, similarities between the respective devices and an identification target need to be calculated as numerical values of 10, 80, and 90, respectively. On the other hand, in classification processing using software of supervised learning, which is one of the machine learning, a relative amount, in which the sum of degrees of certainty (extents of certainty) classified into candidate labels (device A, device B, and device C in this example) is 100%, is calculated. For example, values of 10%, 40%, and 50% are obtained for the three candidates, respectively. That is, while such values can indicate superiority or inferiority in the population, it is impossible to determine, as absolute amounts, how similar the candidates and the identification target are, by using the values. Due to this, with simple application of machine learning, it is impossible to determine a new type by the new type determination threshold.

A second problem is a problem related to presetting of a new type determination threshold. An appropriate new type determination threshold is different depending on how many similar devices are present in a network environment. For example, even if an identification target is actually a new type device, when there are a large number of devices of the same type in the environment, the degree of similarity with existing devices is calculated to be high, and thus the new type determination threshold has to be set to be high in order to correctly determine a new type. On the other hand, if the new type determination threshold is too high, the same device cannot be correctly determined. This is because communication information such as a packet length has a variation and thus even feature amounts obtained from the same devices do not become exactly identical. In a situation where it is not clear what type of devices are connected, it is difficult to automatically set an appropriate threshold.

The present invention is made in light of the foregoing, and an object of the present invention is to enable highly accurate determination of a type or a model of a device connected to a network or whether the device is a new type, by machine learning.

Means for Solving the Problem

A device identification apparatus according to the present invention includes: a communication information collection unit configured to acquire communication information on existing devices indicating devices that exist and are connected to a network in models or types and acquire communication information on an identification target device indicating a device to be identified; a feature amount generation unit configured to make the communication information of the existing devices feature amounts at a predetermined time interval, and generate feature amount data by assigning labels for identifying the models or the types to the feature amounts to use the feature amount data as first training data, make the communication information of the identification target device feature amounts at a predetermined time interval, and generate feature amount data by assigning a dummy label to the feature amounts to use the feature amount data as second training data, and further acquire communication information of the identification target device, make the communication information feature amounts at a predetermined time interval to generate feature amount data, and use the generated feature amount data as identification data; a machine learning unit configured to cause a learning engine to learn the first training data with the labels and the second training data with the dummy label, and input the identification data to the learning engine that has learned the first training data and the second training data to classify the feature amount data of the identification target device into the labels including the dummy label; a degree-of-similarity calculation unit configured to calculate, based on the number of pieces of the feature amount data classified into the labels and the number of pieces of the feature amount data classified into the dummy label, a degree of similarity between a model or a type of the identification target device and each of the models or types indicated by the labels; and a device identification unit configured to determine, for the degree of similarity of each of the labels, whether there is a label having a degree of similarity equal to or greater than a predetermined new type determination threshold, in accordance with a determination that there is a label having a degree of similarity equal to or greater than the predetermined new type determination threshold, identify the identification target device as an existing device of a model or type indicated by the label, and in accordance with a determination that there is no label having a degree of similarity equal to or greater than the predetermined new type determination threshold, identify the identification target device as a new type device different from the models or types indicated by the existing labels.

Effects of the Invention

According to the present invention, it is possible to determine a type or model of a device connected to a network or whether the device is a new type with high accuracy by machine learning.

BRIEF DESCRIPTION OF DRAWINGS

FIG. 3 is a diagram for explaining calculation of a degree of similarity for each label (model) according to the device identification apparatus (degree-of-similarity calculation unit) according to the present embodiment.

DESCRIPTION OF EMBODIMENTS

Next, an embodiment of the present invention (hereinafter referred to as "present embodiment") will be described.

Figure 1:
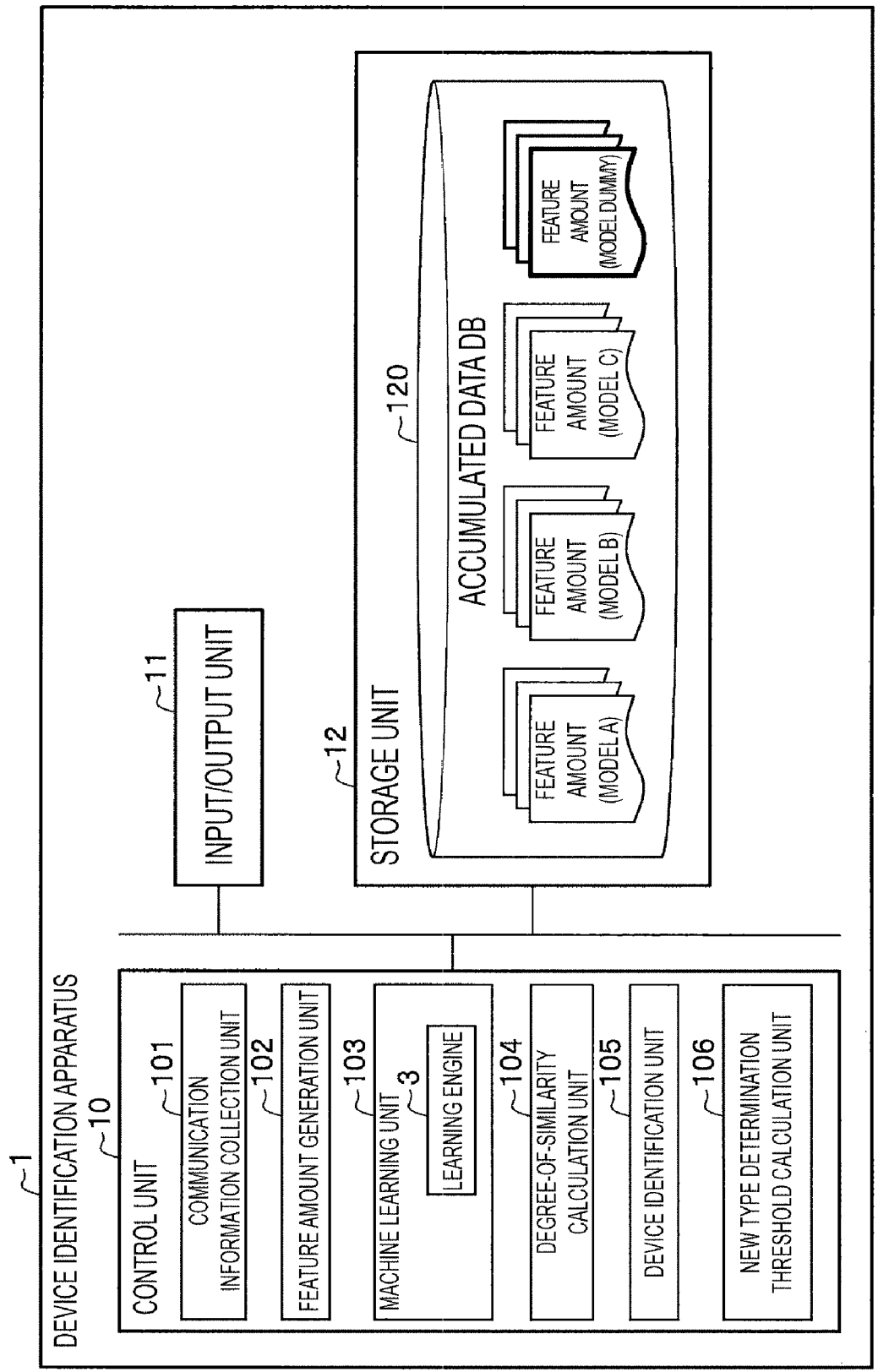
FIG. 1 is a block diagram illustrating a configuration of a device identification apparatus according to a present embodiment.

FIG. 1 is a block diagram illustrating a configuration of a device identification apparatus 1 according to the present embodiment.

The device identification apparatus 1 acquires communication information of devices that are communicatively connected via a network, and the like, and determines whether a device to be identified is a new type device (new model (or class) that does not exist as models (or classes) of devices that exist).

The device identification apparatus 1 performs <1> calculation of a degree of similarity of a device to be identified by using machine learning and <2> automatic setting of a new type determination threshold to implement a determination of whether the device is a new type device. Note that in the present embodiment described below, the description will be mainly given on the premise that the device identification apparatus 1 determines a "model" of a device to be identified. However, the device identification apparatus 1 can also determine a "class" of the identification target device by a similar technique.

In calculating a degree of similarity of a device, the device identification apparatus 1 assigns a new label (dummy label) different from labels assigned to feature amount data of communication information of models accumulated until then to feature amount data (details will be described later) of communication information of a device to be identified, and uses the data with the new label as training data to train a learning engine. The device identification apparatus 1 then uses, as a degree of similarity of a device, a value obtained by dividing the number of feature amounts (the number of pieces of feature amount data) classified into each label by the number of feature amounts classified into the dummy label, the resulting value being expressed in percentage. In addition, the device identification apparatus 1 calculates the degree of similarity under two conditions, that is, when there is training data corresponding to the device to be identified and when the training data does not exist, and calculates a new type determination threshold from the calculated degrees of similarity under the two conditions (details will be described later).

In this way, the device identification apparatus 1 automatically calculates a new type determination threshold for identifying a new type device on the basis of communication information of devices. Then, the device identification apparatus 1 compares the value of the degree of similarity calculated based on the communication information of the device to be identified and the communication information of devices already accumulated with the new type determination threshold, so that it is possible to determine whether the device to be identified is a new type device.

Next, functions of the device identification apparatus 1 will be specifically described with reference to FIG. 1.

The device identification apparatus 1 is realized by a computer including a control unit 10, an input/output unit 11, and a storage unit 12.

The input/output unit 11 is composed of a communication interface for transmitting and receiving information, and an input/output interface for transmitting and receiving information to and from an input apparatus such as a touch panel and a keyboard and an output apparatus such as a monitor.

The storage unit 12 is composed of a flash memory, a hard disk, a random access memory (RAM), and the like. In the storage unit 12 of the device identification apparatus 1, information of feature amounts extracted from communication information of devices, to which a label is assigned for each model (or class), is stored in an accumulated data database (DB) 120.

As illustrated in FIG. 1, the control unit 10 includes a communication information collection unit 101, a feature amount generation unit 102, a machine learning unit 103, a degree-of-similarity calculation unit 104, a device identification unit 105, and a new type determination threshold calculation unit 106.

The communication information collection unit 101 acquires communication information in models of devices. Here, the communication information is information obtained by collecting information such as a packet length of a packet transmitted and received by each device in the network, a destination port number, or a window size of a header for a predetermined period of time (e.g., 10 minutes). Note that when the communication information collection unit 101 acquires communication information in classes of devices, the communication information collection unit 101 also acquires information similar to that in models (e.g., packet length, destination port number, window size, and the like).

The communication information collection unit 101 may acquire the communication information directly from devices, or may acquire the communication information from a network management apparatus (not illustrated) or the like that manages the devices.

When a device to be identified (hereinafter, sometimes referred to as an "identification target device") is connected to the network, the communication information collection unit 101 collects communication information transmitted and received by the identification target device for a predetermined period of time (e.g., 10 minutes). Note that the communication information collection unit 101 collects the communication information of the identification target device for collecting training data and for collecting identification data.

Note that the communication information collection unit 101 acquires information that the identification target device is connected to the network, for example, from the network management apparatus or the like. Furthermore, the communication information collection unit 101 may acquire the communication information of the identification target device in two separate timings for the training data and for the identification data, and may acquire the communication information continuously for the training data and for the identification data and divide the acquired information.

The feature amount generation unit 102 acquires the communication information of existing (identified) devices, and performs the following processing.

The feature amount generation unit 102 makes the communication information in models of devices acquired for a predetermined period of time (e.g., 10 minutes) feature amounts (for example, calculates an average value) at a predetermined time interval (a predetermined cycle, e.g., 60 seconds cycle) and assigns labels to the feature amounts to generate the feature amount data (communication information made feature amounts). Then, the feature amount generation unit 102 stores the feature amount data with labels as training data (first training data) in the accumulated data DB 120 in the storage unit 12. Here, the labels are information identifying models (or classes), and for example, Model A, Model B, and Model C are assigned as the labels (existing labels).

Note that the processing described above by the feature amount generation unit 102 is performed in advance before processing the communication information of the identification target device.

Furthermore, the feature amount generation unit 102 acquires the communication information of the identification target device, and performs the following processing. When the feature amount generation unit 102 acquires the communication information of the identification target device for a predetermined period of time (for example, 10 minutes), the feature amount generation unit 102 makes the communication information feature amounts at a predetermined time interval (for example, 60 second s cycle) and assigns a dummy label to the feature amounts to and generate the feature amount data. Then, the feature amount generation unit 102 stores the feature amount data with the dummy label as training data (second training data) in the accumulated data DB 120 in the storage unit 12.

Furthermore, when the feature amount generation unit 102 further acquires the communication information of the identification target device for a predetermined period of time (for example, 10 minutes), the feature amount generation unit 102 makes the communication information feature amounts at a predetermined time interval (for example, 60 seconds cycle) to generate feature amount data. The feature amount generation unit 102 stores the feature amount data as identification data in the storage unit 12.

The machine learning unit 103 includes a learning engine 3 (machine learning algorithm). As the machine learning algorithm, a neural network, a logistic regression, a support vector machine (SVM), or the like can be used, for example.

The machine learning unit 103 causes the learning engine 3 to learn training data (feature amount data) with labels (models) of devices. In addition, the machine learning unit 103 causes the learning engine 3 to learn the feature amount data with the dummy label of the identification target device as the training data.

In addition, the machine learning unit 103 inputs feature amount data to be identified (identification data) to the learning engine 3, the feature amount data being obtained by making the communication information of the identification target device feature amounts, and classifies the feature amount data into labels (including the dummy label).

Figure 2:
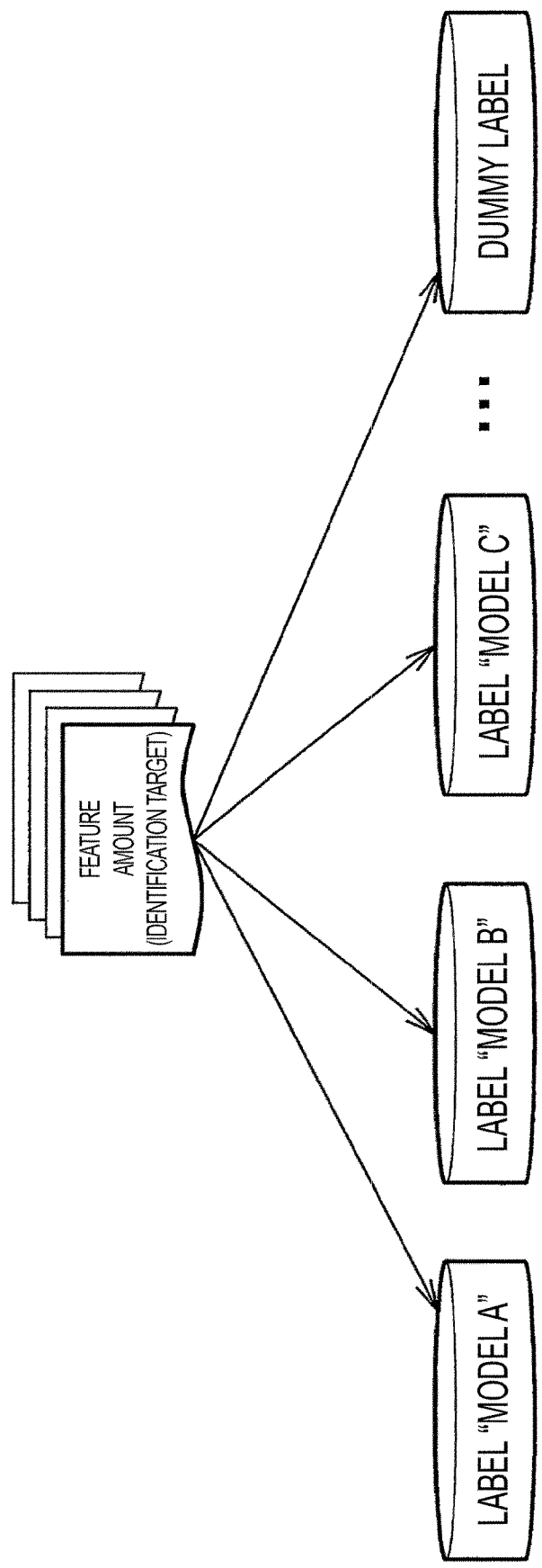
FIG. 2 is a diagram for explaining processing of classifying feature amount data of an identification target device into labels (including a dummy label) by the device identification apparatus (machine learning unit) according to the present embodiment.

As a result, as illustrated in FIG. 2, the feature amount data (identification data) of the identification target device is classified into the label "Model A", the label "Model B", the label "Model C", or the dummy label.

With reference again to FIG. 1, the degree-of-similarity calculation unit 104 performs calculation in which based on the number of pieces of the feature amount data classified into each label by the machine learning unit 103, the number of pieces of the feature amount data classified into a label (existing label) other than the dummy label is divided by the number of pieces of the feature amount data classified into the dummy label and the resulting value is expressed in percentage to be used as a degree of similarity of the device.

For example, as illustrated in FIG. 3, when the number of pieces of the feature amount data classified into the dummy label is "6", the number of pieces of the feature amount data classified into Model A is "1", the number of pieces of the feature amount data classified into Model B is "0", and the number of pieces of the feature amount data classified into Model C is "5," degrees of similarity of the models indicated by the respective labels are calculated as follows.

Degree of similarity of label "Model A" . . . 1/6×100=17%
Degree of similarity of label "Model B" . . . 0/6×100=0%
Degree of similarity of label "Model C" . . . 5/6×100=83%

As a result, when training data of a model corresponding to the identification target device is already present, half of the feature amount data is theoretically classified into each of the dummy label and a label (model) of a corresponding existing device, resulting in a degree of similarity of near 100%. On the other hand, when there is no training data of the model corresponding to the identification target device, almost all the feature amount data (identification data) is classified into the dummy label, resulting in a very small value even in a degree of similarity of the label (model) corresponding to the most similar device.

With reference again to FIG. 1, the device identification unit 105 uses a new type determination threshold calculated by the new type determination threshold calculation unit 106 described later to determine whether or not there is a label (model) indicating a degree of similarity equal to or greater than the new type determination threshold, among the values of degrees of similarity of the labels calculated by the degree-of-similarity calculation unit 104. Then, when there is a label (model) indicating a degree of similarity equal to or greater than the new type determination threshold, the device identification unit 105 determines that the identification target device is a device of the model (the same model as the model of an existing device).

On the other hand, when there is no model indicating a degree of similarity equal to or greater than the new type determination threshold, the device identification unit 105 determines that the identification target device with the dummy label is a new type device (for example, "Model D").

Note that when the device identification unit 105 determines that the identification target device is a new type device, the device identification unit 105 outputs this information to the new type determination threshold calculation unit 106. As a result, the new type determination threshold calculation unit 106 executes the new type determination threshold calculation processing again, and updates the new type determination threshold.

When the device identification unit 105 determines that the identification target device is a new type device, the new type determination threshold calculation unit 106 executes the new type determination threshold calculation processing to calculate and update the new type determination threshold.

The new type determination threshold is a threshold for the degree of similarity, which is provided for determining whether the identification target device is a new type (new model) for which there is no accumulated data for learning (training data), or of an existing model for which there is already training data. A method for calculating a new type determination threshold by the new type determination threshold calculation unit 106 will be described below.

Note that the communication information collection unit 101 collects communication information transmitted and received for a predetermined period of time (e.g., 10 minutes) from any number (number of models, e.g., Model A, Model B, Model C) of devices in advance. Then, the feature amount generation unit 102 makes the communication information in models feature amounts (for example, calculates an average value) at a predetermined time interval (predetermined cycle, e.g., 60 seconds cycle) to generate feature amount data, assigns labels (e.g., Model A, Model B, Model C) to the feature amount data, and stores the feature amount data with labels in the storage unit 12.

For example, the feature amount generation unit 102 acquires, from the communication information collection unit 101, data (communication information) captured for 10 minutes for each device, and makes the data (communication information) a feature amount at 60 seconds cycle to generate 10 pieces of feature amount data per device (model).

Note that instead of newly generating the feature amount data for each model, the new type determination threshold calculation unit 106 may use the feature amount data of each model stored in the accumulated data DB 120 for the new type determination threshold calculation processing.

In the above-described state, the new type determination threshold calculation unit 106 divides the feature amount data of each model into training data and test data. The division ratio is arbitrary, but in general machine learning, it is often set to be 80% of training data and 20% of test data.

Next, the new type determination threshold calculation unit 106 performs learning by the machine learning unit 103 (learning engine 3) using the training data of all the labels (models). Then, degrees of similarity for devices of the labels (models) are calculated by the same procedure as the degree of similarity calculation processing described above.

Specifically, the new type determination threshold calculation unit 106 selects one label (model) and divides the test data of the model into two. The division ratio is arbitrary, but the test data is divided, for example, in half. The new type determination threshold calculation unit 106 assigns a dummy label to one of the divided pieces of the test data and causes the learning engine 3 to learn the test data with the dummy label. Then, the new type determination threshold calculation unit 106 inputs the remaining piece of the test data to the learning engine 3, and classifies the input test data into labels (including the dummy label).

Subsequently, similarly to the processing of the degree-of-similarity calculation unit 104, the new type determination threshold calculation unit 106 performs calculation in which based on the number of pieces of the feature amount data classified into each label, the number of pieces of the feature amount data classified into a label is divided by the number of pieces of the feature amount data classified into the dummy label and the resulting value is expressed in percentage to be used as a degree of similarity of the device.

Then, the new type determination threshold calculation unit 106 extracts the degree of similarity of a correct (selected) label (model) as the "degree of similarity of the device when there is training data". The new type determination threshold calculation unit 106 performs this processing while selecting each of all models to extract a degree of similarity of a correct label (model) when there is training data.

Next, the new type determination threshold calculation unit 106 excludes training data belonging to one label arbitrarily selected among all the training data and performs learning by the learning engine 3. Then, the new type determination threshold calculation unit 106 calculates degrees of similarity for devices of respective models by the same procedure as the degree of similarity calculation processing described above.

Specifically, for one selected label, the new type determination threshold calculation unit 106 divides test data for the label (model) into two. The division ratio is arbitrary, but the test data is divided, for example, in half. The new type determination threshold calculation unit 106 assigns a dummy label to one of the divided pieces of the test data and causes the learning engine 3 to learn the test data with the dummy label. Then, the new type determination threshold calculation unit 106 inputs the remaining piece of the test data to the learning engine 3, and classifies the input test data into labels (including the dummy label).

Subsequently, similarly to the degree-of-similarity calculation unit 104, the new type determination threshold calculation unit 106 performs calculation in which based on the number of pieces of the feature amount data classified into each label, the number of pieces of the feature amount data classified into a label is divided by the number of pieces of the feature amount data classified into the dummy label and the resulting value is expressed in percentage to be used as a degree of similarity of the device.

Then, the new type determination threshold calculation unit 106 extracts a degree of similarity of the most similar label among degrees of similarity of labels when there is no training data. The new type determination threshold calculation unit 106 also performs similar processing for all other labels, and extracts the "degree of similarity of the most similar device when there is no training data".

Figure 4:
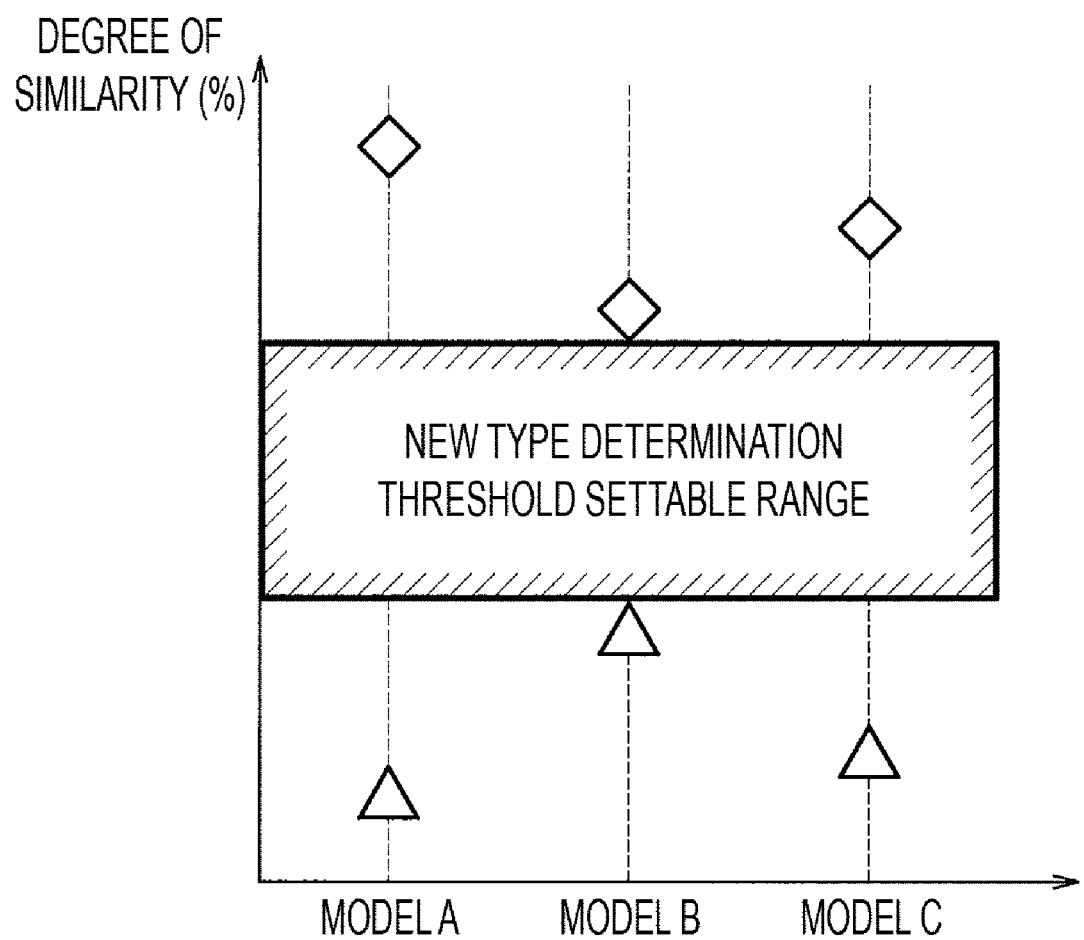
FIG. 4 is a diagram for explaining setting of a new type determination threshold (new type determination threshold settable range) by the device identification apparatus (new type determination threshold calculation unit) according to the present embodiment.

The new type determination threshold calculation unit 106 sets a new type determination threshold for each model, extracted above process, so as to fall between the "degree of similarity of the device when there is training data" and the "degree of similarity of the most similar device when there is no training data" (see FIG. 4). Note that in FIG. 4, a symbol "◊" indicates a degree of similarity with a correct label when there is training data ("p" described below). Furthermore, a symbol "Δ" indicates a degree of similarity of the most similar device when there is no training data ("q" described below). As illustrated in FIG. 4, in all of Model A, Model B, and Model C, a range that falls between the "degree of similarity of a device when there is training data" (◊) and the "degree of similarity of the most similar device when there is no training data" (Δ) is ideally a new type determination threshold settable range.

Specifically, a new type determination threshold is calculated, for example, so that an intermediate value between the degree of similarity of a device when there is training data and the degree of similarity of the most similar device when there is no training data satisfies new type determination threshold calculation equations of Equations (1) and (2) which will be described below.

This is because it is not possible to ensure that there is a similar tendency for degrees of similarity also in an actual device of new type and thus, when a margin is widely left on either side of new type determination and existing type determination, that is, an intermediate value is taken, it is possible to absorb these factors.

[Math. 1]

$$F(x) = \sum_{i=1}^{n} (|(p_i - x) - (x - q_i)|) \quad \text{Equation (1)}$$

$$x = \mathrm{argmin} F(x) \quad \text{Equation (2)}$$

Where x is a new type determination threshold, p is a degree of similarity with a correct label when there is training data, q is a degree of similarity of the most similar device when there is no training data, and n is the number of labels. In addition, Equation (2) is meant to calculate x that minimizes F(x).

Figure 5:
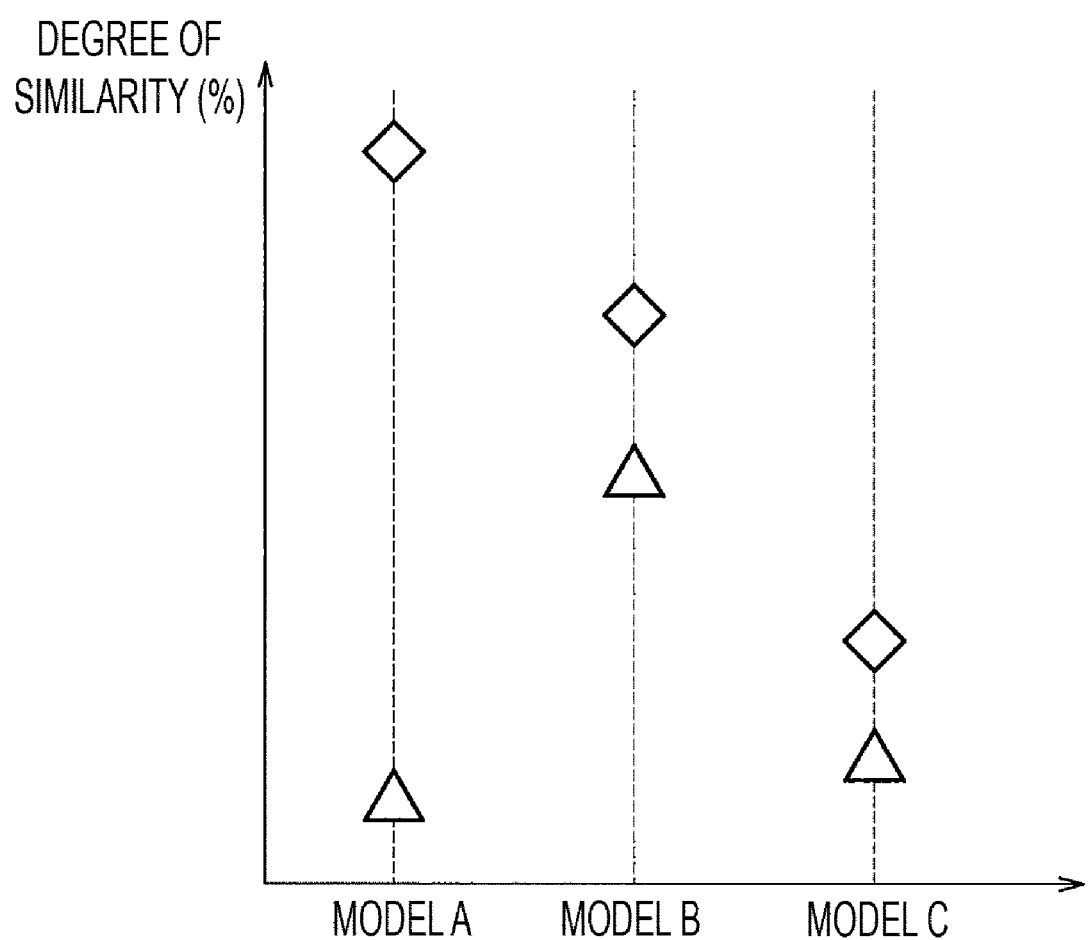
FIG. 5 is a diagram for explaining a problem of the setting of a new type determination threshold by the device identification apparatus (new type determination threshold calculation unit) according to the present embodiment.

In addition, calculated degrees of similarity vary from model to model and thus, it may be impossible to set a new type determination threshold that satisfies the conditions for all models (see FIG. 5). In other words, in FIG. 4, a common new type determination threshold settable range can be provided for all the models. On the other hand, in the example illustrated in FIG. 5, settable ranges do not overlap for Model B and Model C and it is thus impossible to simply set a new type determination threshold.

In such a case as well, the new type determination threshold calculation unit 106 sets a new type determination threshold by the technique using Equation (1) and Equation (2) as described above, so that a new type determination threshold capable of performing correct identification for as many models as possible can be calculated.

Figure 6:
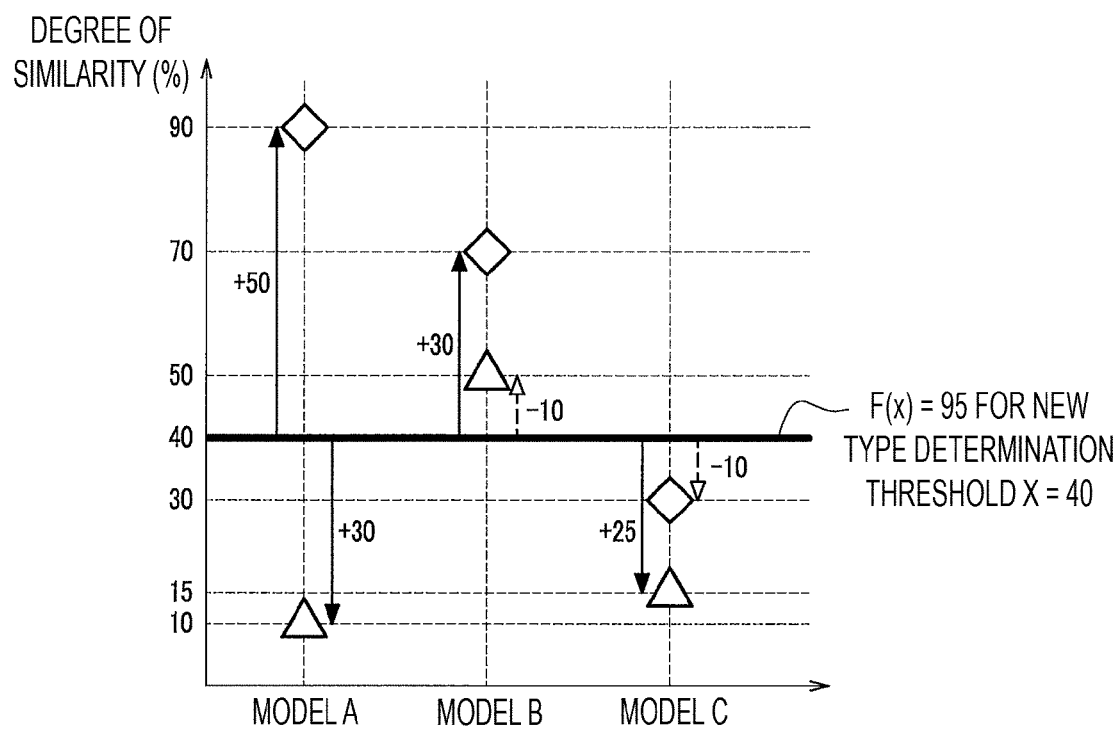
FIG. 6 is a diagram for explaining a specific example of calculation of a new type determination threshold by the device identification apparatus (new type determination threshold calculation unit) according to the present embodiment.
Figure 7:
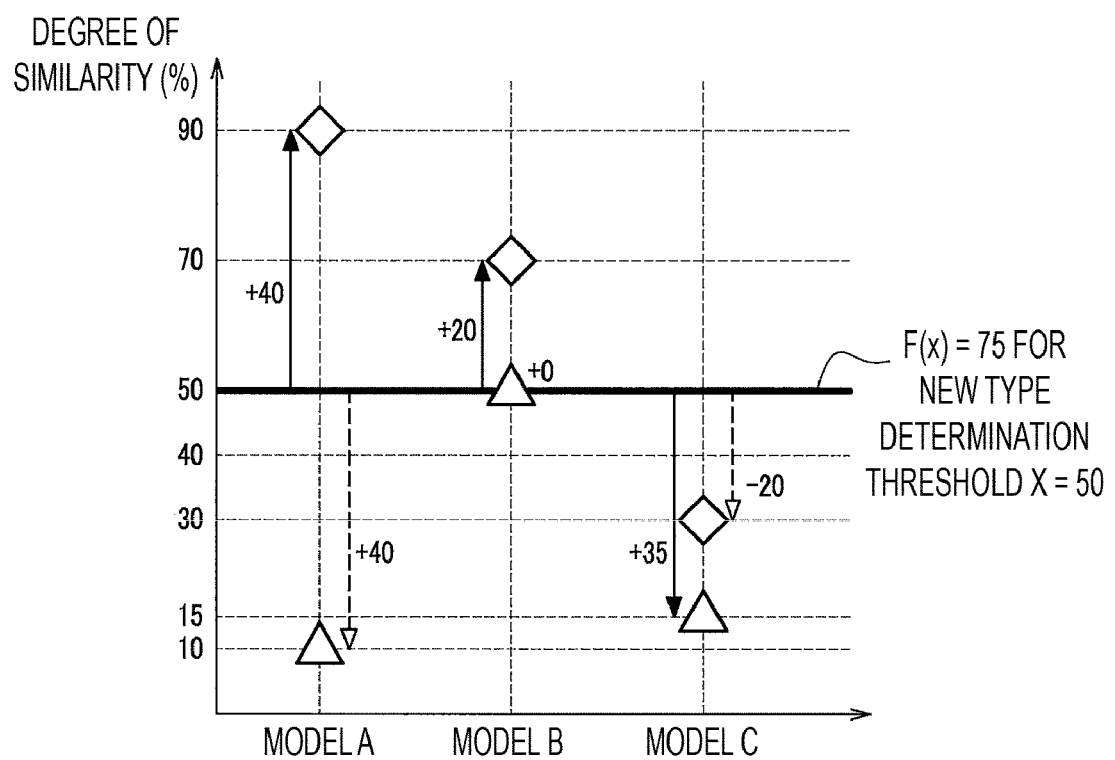
FIG. 7 is a diagram for explaining a specific example of calculation of a new type determination threshold by the device identification apparatus (new type determination threshold calculation unit) according to the present embodiment.
Figure 8:
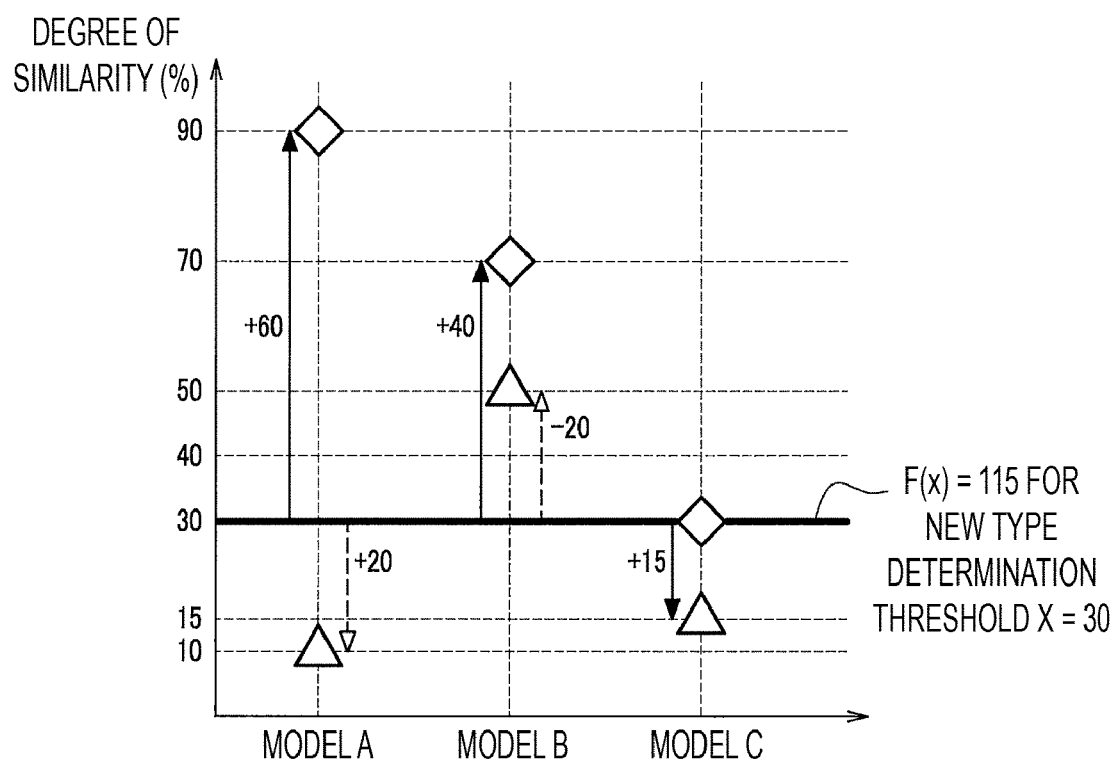
FIG. 8 is a diagram for explaining a specific example of calculation of a new type determination threshold by the device identification apparatus (new type determination threshold calculation unit) according to the present embodiment.

FIGS. 6 to 8 are diagrams for conceptually explaining processing in which the new type determination threshold calculation unit 106 calculates a new type determination threshold using Equation (1) and Equation (2) described above.

Here, it is assumed that the degree of similarity (p) with a correct label when there is training data for Model A is "90 (%)" and the degree of similarity (q) of the most similar device when there is no training data for Model A is "10 (%)". In addition, it is assumed that the degree of similarity (p) with a correct label when there is training data for Model B is "70 (%)" and the degree of similarity (q) of the most similar device when there is no training data for Model B is "50 (%)". In addition, it is assumed that the degree of similarity (p) with a correct label when there is training data for Model C is "30 (%)" and the degree of similarity (q) of the most similar device when there is no training data for Model C is "15 (%)".

In a case where the new type determination threshold x=40 holds as illustrated in FIG. 6, when $(|(p_i-x)-(x-q_i)|)$ of Equation (1) is calculated for each model, the following values are obtained.
Model A: (|(90−40)−(40−10)|)=20
Model B: (|(70−40)−(40−50)|)=40
Model C: (|(30−40)−(40−15)|)=35

Thus, F(x)=20+40+35=95 is obtained.

Similarly, FIG. 7 illustrates a case where the new type determination threshold x=50 holds, and F(x)=75 is obtained. Furthermore, FIG. 8 illustrates a case where the new type determination threshold x=30 holds, and F(x)=115 is obtained.

The new type determination threshold calculation unit 106 can determine the new type determination threshold x that minimizes F(x) by searching in this manner.

Note that as described above, when the device identification unit 105 determines that an identification target device is a new type device based on the new type determination threshold, the new type determination threshold calculation unit 106 adds the device to existing devices, performs similar processing (new type determination threshold calculation processing), and updates the new type determination threshold.

Flow of Processing

Next, a flow of processing executed by the device identification apparatus 1 will be described.

Device Identification Processing

Figure 9:
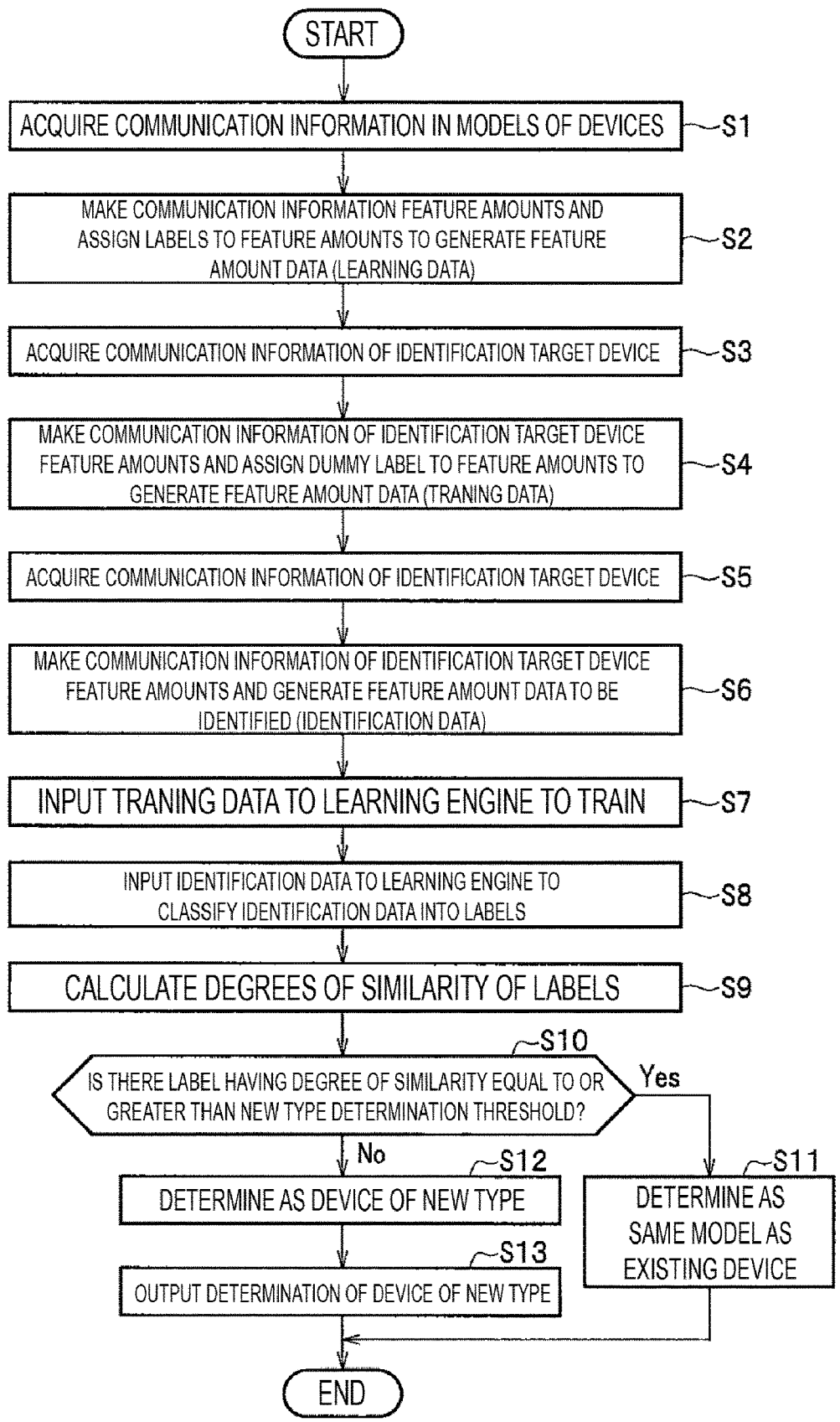
FIG. 9 is a flowchart of device identification processing executed by the device identification apparatus according to the present embodiment.

FIG. 9 is a flowchart illustrating device identification processing executed by the device identification apparatus 1 according to the present embodiment. The device identification apparatus 1 utilizes machine learning to calculate a degree of similarity based on a feature amount of a device to be identified and feature amounts of models corresponding to existing devices, and compares the calculated degree of similarity with a new type determination threshold to determine whether the identification target device is a device of the same model as the existing models or a new type device. Detailed description will be given below.

First, the communication information collection unit 101 of the device identification apparatus 1 acquires communication information in models of devices (step S1). The communication information collection unit 101 acquires the communication information of the devices for a predetermined period of time (for example, 10 minutes) in models.

Next, the feature amount generation unit 102 makes the communication information in models of the devices collected by the communication information collection unit 101 feature amounts at a predetermined time interval (for example, 60 seconds cycle), and assigns labels of models of the devices (e.g., Model A, Model B, Model C) to the feature amounts to generate feature amount data (training data) (step S2). Then, the feature amount generation unit 102 stores the feature amount data with labels as training data (first training data) in the accumulated data DB 120 in the storage unit 12.

Note that steps S1 and S2 are performed in advance before communication information of the identification target device is acquired.

Next, the communication information collection unit 101 collects communication information transmitted and received by the identification target device for a predetermined period of time (e.g., 10 minutes) when, for example, the identification target device is connected to the network (step S3).

Subsequently, the feature amount generation unit 102 makes the communication information of the identification target device feature amounts at a predetermined time interval (e.g., 60 seconds cycle), and assigns a dummy label to the feature amounts to generate feature amount data (training data) (step S4). Then, the feature amount generation unit 102 stores the feature amount data with the dummy label as training data (second training data) in the accumulated data DB 120 in the storage unit 12.

Next, the communication information collection unit 101 further collects communication information transmitted and received by the identification target device for a predetermined period of time (e.g., 10 minutes) (step S5).

Then, the feature amount generation unit 102 makes the communication information of the identification target device feature amounts at a predetermined time interval (e.g., 60 seconds cycle), and generates feature amount data to be identified (identification data) (step S6). The feature amount generation unit 102 stores the generated feature amount data as the identification data in the storage unit 12.

Subsequently, the machine learning unit 103 inputs the training data which is the feature amount data with the labels of the existing models (Model A, Model B, Model C) and with the dummy label generated by the feature amount generation unit 102 to the learning engine 3 and causes the learning engine 3 to learn the training data (step S7). That is, by inputting the feature amount data and the labels assigned thereto as input data to the learning engine 3, learning is performed in which a parameter of the learning engine 3 is adjusted so that when feature amount data is input, the feature amount data is classified into a correct label.

Then, the machine learning unit 103 inputs the feature amount data to be identified (identification data), which is obtained by making the communication information of the identification target device feature amounts, to the learning engine 3, and classifies the identification data into the labels (including the dummy label) (step S8).

Next, the degree-of-similarity calculation unit 104 calculates degrees of similarity between the model (label) of the identification target device and the models (labels) of the devices based on the number of pieces of the feature amount data classified into the labels (including the dummy label) (step S9).

Specifically, the degree-of-similarity calculation unit 104 performs calculation in which the number of pieces of the feature amount data classified into each label (existing label) other than the dummy label is divided by the number of pieces of the feature amount data classified into the dummy label and the resulting value is expressed in percentage to be used as a degree of similarity of the device (model).

Figure 10:
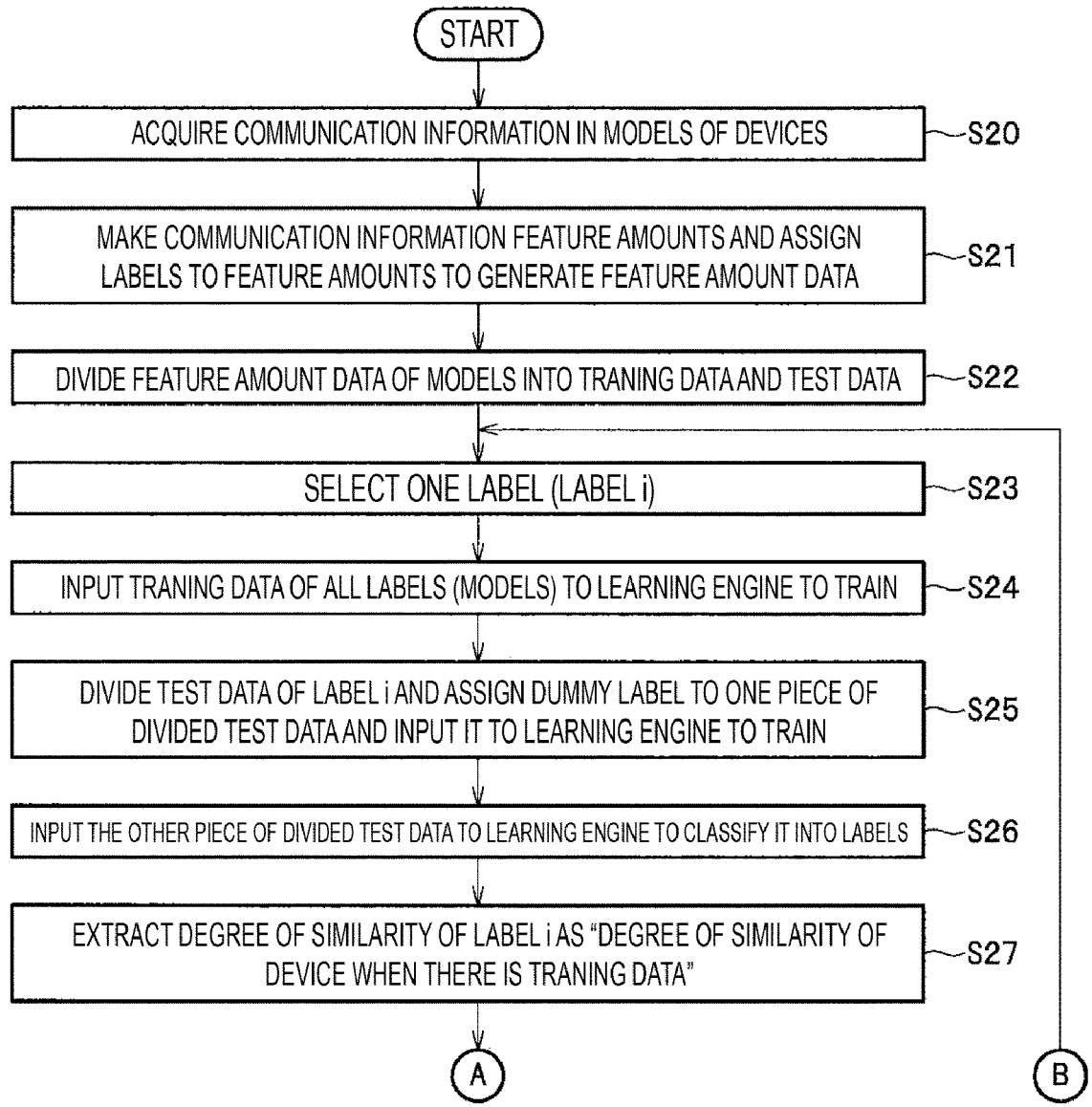
FIG. 10 is a flowchart (1) of new type determination threshold calculation processing executed by the device identification apparatus according to the present embodiment.

Subsequently, the device identification unit 105 uses a new type determination threshold calculated by the new type determination threshold calculation unit 106 performing new type determination threshold calculation processing illustrated in FIG. 10 and FIG. 11 described later to determine whether or not the identification target device is a new type device. Specifically, the device identification unit 105 determines whether or not there is a label (model) indicating a degree of similarity equal to or greater than the new type determination threshold, among values indicating the degrees of similarity of the labels calculated by the degree-of-similarity calculation unit 104 (step S10).

Then, in accordance with a determination that there is a label (model) indicating a degree of similarity equal to or greater than the new type determination threshold (step S10→Yes), the device identification unit 105 determines that the model indicated by the label is the model of the identification target device. That is, the device identification unit 105 determines that the identification target device is of the same model as the existing device (step S11).

On the other hand, in accordance with a determination that there is no label (model) indicating a degree of similarity equal to or greater than the new type determination threshold (step S10→No), the device identification unit 105 determines the identification target device with the dummy label as a new type device (step S12).

Then, the device identification unit 105 outputs the information, to the new type determination threshold calculation unit 106, that the identification target device is determined to be a new type device (step S13) and ends the processing.

As a result, the new type determination threshold calculation unit 106 adds the identification target device determined to be a new type device to the existing devices as, for example, Model D, and executes the new type determination threshold calculation processing again to update the new type determination threshold.

In this way, the device identification apparatus 1 uses the feature amount data generated from communication information of devices and determines labels by machine learning, so that it is possible to classify a corresponding label of the feature amount data with higher accuracy. Furthermore, the device identification apparatus 1 can determine, for an identification target device connected to a network, whether the device is of an existing model (or type) or of a new type, using a degree of similarity that is an absolute amount calculated based on the number of pieces of the feature amount data classified by the learning engine 3 rather than a relative amount between labels into which devices are classified.

New Type Determination Threshold Calculation Processing

Next, new type determination threshold calculation processing by the new type determination threshold calculation unit 106 of the device identification apparatus 1 will be described. FIG. 10 and FIG. 11 are flowcharts each illustrating the new type determination threshold calculation processing executed by the device identification apparatus 1 according to the present embodiment.

Note that the new type determination threshold calculation processing by the new type determination threshold calculation unit 106 is started when information is acquired from the device identification unit 105 that the identification target device is determined to be a new type device at step S13 in FIG. 9.

First, the new type determination threshold calculation unit 106 of the device identification apparatus 1 acquires communication information in models of devices through the communication information collection unit 101 (step S20). The new type determination threshold calculation unit 106 acquires the communication information in models of the devices for a predetermined period of time (for example, 10 minutes). Here, in the device identification processing in FIG. 9, the communication information of the devices is acquired in a state where the identification target device determined to be a new type device is added as, for example, Model D to existing devices.

Next, the new type determination threshold calculation unit 106 makes the collected communication information in models of the devices feature amounts through the feature amount generation unit 102 at a predetermined time interval (for example, 60 seconds cycle), and assigns labels of models of the devices (e.g., Model A, Model B, Model C, Model D) to the feature amounts to generate feature amount data (step S21). Then, the new type determination threshold calculation unit 106 stores the feature amount data with labels in the storage unit 12 through the feature amount generation unit 102.

Next, the new type determination threshold calculation unit 106 divides the feature amount data of the models into training data and test data (step S22). For example, the new type determination threshold calculation unit 106 divides the feature amount data into 80% of training data and 20% of test data.

Next, the new type determination threshold calculation unit 106 selects one label (model) (step S23). Note that the label selected here is referred to as "label i". Then, the new type determination threshold calculation unit 106 uses the test data of the label i to calculate a degree of similarity between the label i and another label (model) in accordance with the same procedure as the degree of similarity calculation processing described above.

Specifically, first, the new type determination threshold calculation unit 106 inputs the training data with labels for all the models (Model A, Model B, Model C, Model D) to the learning engine 3 and causes the learning engine 3 to learn the training data (step S24).

Next, the new type determination threshold calculation unit 106 divides the test data for the selected label i into two, assigns a dummy label to one of the divided pieces of the test data (feature amount data), inputs the test data with the dummy label to the learning engine 3, and causes the learning engine 3 to learn the test data with the dummy label (step S25).

Next, the new type determination threshold calculation unit 106 inputs the other of the divided pieces of the test data (feature amount data) to the learning engine 3, and classifies the test data into the labels (including the dummy label) (step S26).

Then, the new type determination threshold calculation unit 106 performs calculation in which the number of pieces of the feature amount data classified into each label is divided by the number of the feature amount data classified into the dummy label and the resulting value is expressed in percentage to be used as a degree of similarity of a device. Then, the new type determination threshold calculation unit 106 extracts the degree of similarity of the selected label i as the "degree of similarity of the device when there is training data" (step S27).

Figure 11:
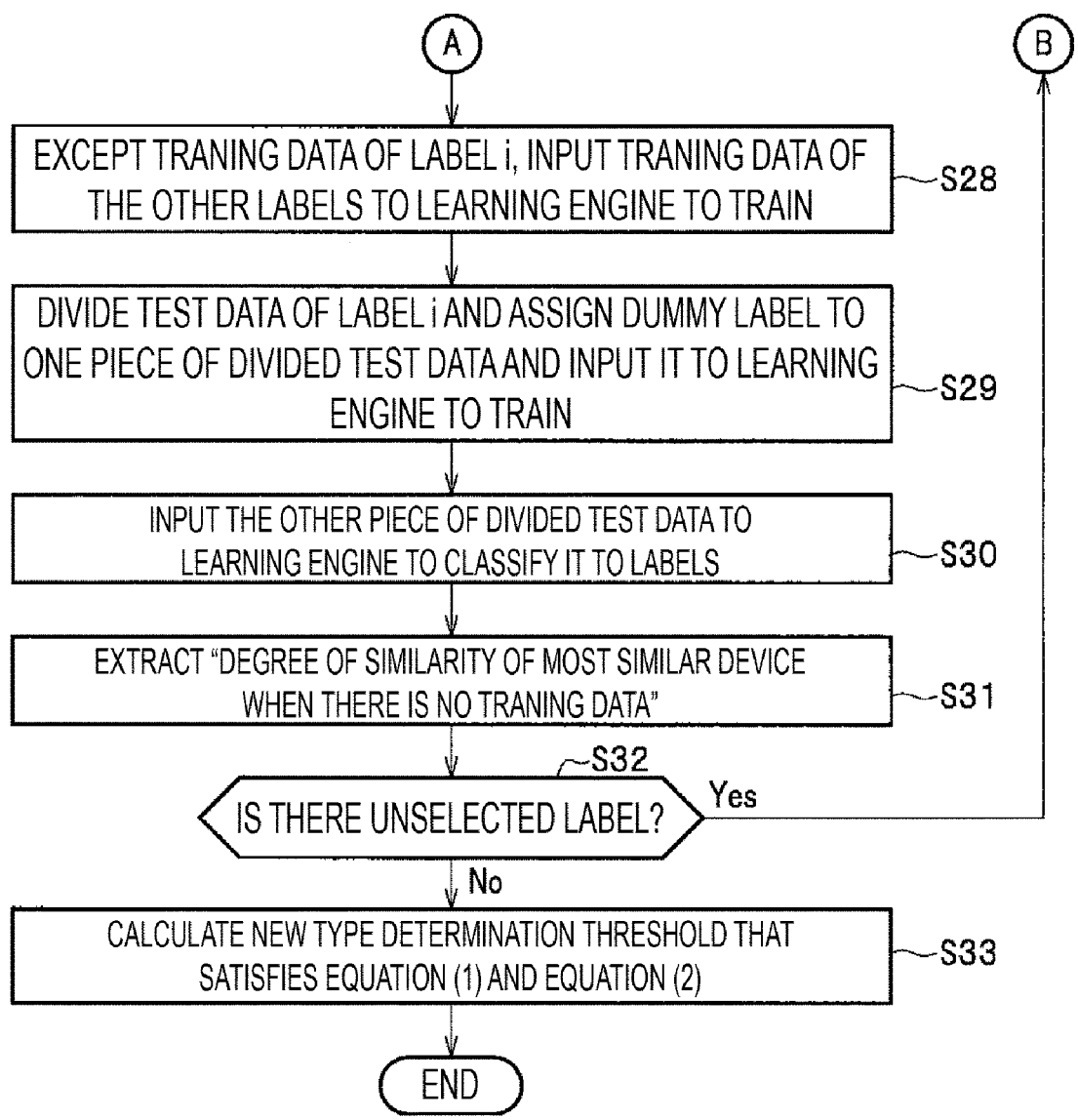
FIG. 11 is a flowchart (2) of the new type determination threshold calculation processing executed by the device identification apparatus according to the present embodiment.

Next, with reference to FIG. 11, the new type determination threshold calculation unit 106 excludes the training data for the selected label i among all the training data, inputs the training data for the remaining labels to the learning engine 3, and causes the learning engine 3 to learn the training data for the remaining labels (step S28).

Then, the new type determination threshold calculation unit 106 divides the test data for the selected label i into two, assigns a dummy label to one of the divided pieces of the test data (feature amount data), inputs the test data with the dummy label to the learning engine 3, and causes the learning engine 3 to learn the test data with the dummy label (step S29).

Subsequently, the new type determination threshold calculation unit 106 inputs the other of the divided pieces of the test data (feature amount data) to the learning engine 3, and classifies the test data into the labels (including the dummy label) (step S30).

Then, the new type determination threshold calculation unit 106 performs calculation in which the number of pieces of the feature amount data classified into each label is divided by the number of the feature amount data classified into the dummy label and the resulting value is expressed in percentage to be used as a degree of similarity of a device. Then, the new type determination threshold calculation unit 106 extracts the degree of similarity of the most similar label among degrees of similarity of the labels as the "degree of similarity of the most similar device when there is no training data" (step S31).

Subsequently, the new type determination threshold calculation unit 106 determines whether or not there is a label that has not yet been selected (step S32). In accordance with a determination that there is a label that has not yet been selected (step S32→Yes), the processing returns to step S23 in FIG. 10 and continues.

On the other hand, in accordance with a determination that all the labels have been selected (step S3→No), the processing proceeds to the next step S33.

In step S33, the new type determination threshold calculation unit 106 uses the "degree of similarity of the device when there is training data" for each extracted model and the "degree of similarity of the most similar device when there is no training data" to calculate a new type determination threshold that satisfies the new type determination threshold calculation equations of Equation (1) and Equation (2) described above, and ends the processing.

In this way, the device identification apparatus 1 according to the present embodiment automatically calculates a new type determination threshold for identifying a new type device based on feature amounts of communication information of devices. The device identification apparatus 1 compares the value of the degree of similarity calculated based on the feature amount of a device to be identified and the feature amounts of devices that have been accumulated in advance with the new type determination threshold, so that it is possible to determine whether or not the device to be identified is a new type device.

Hardware Configuration

Figure 12:
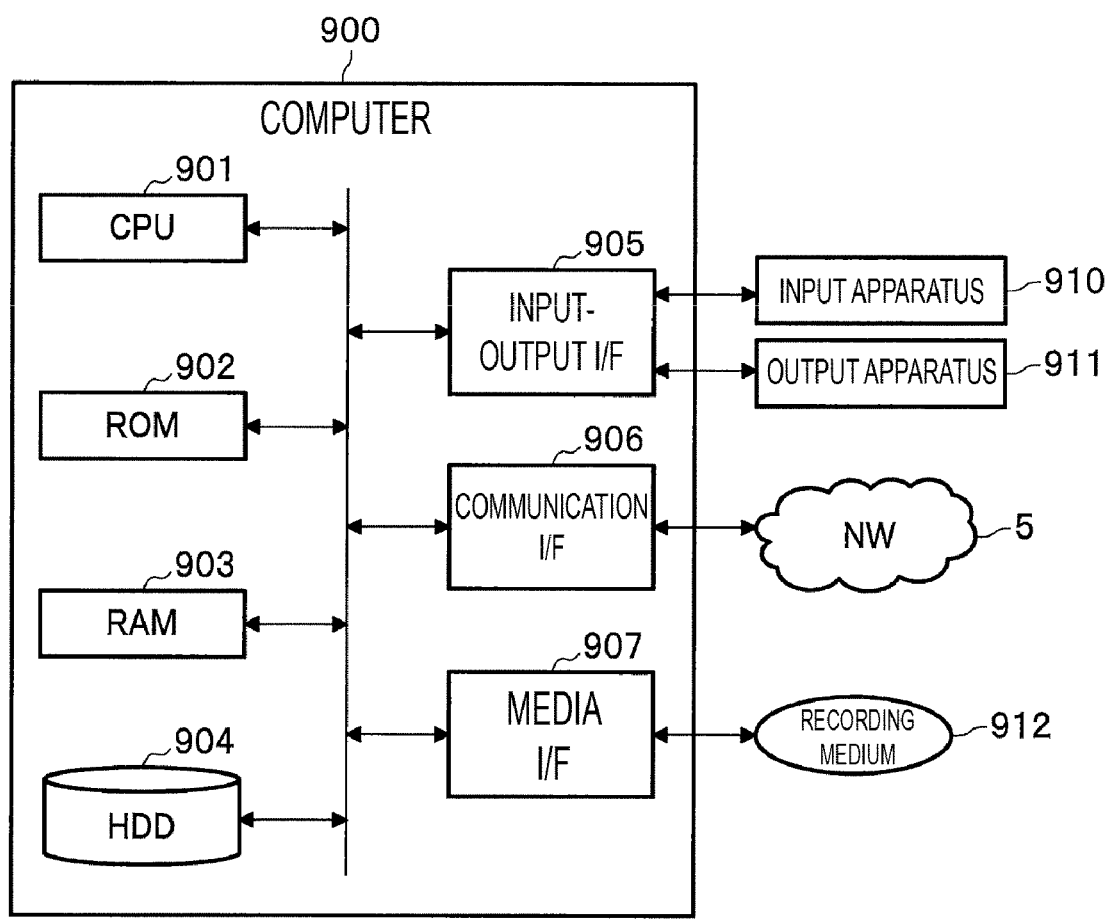
FIG. 12 is a hardware configuration diagram illustrating an example of a computer that implements functions of the device identification apparatus according to the present embodiment.

The device identification apparatus 1 according to the present embodiment is realized by a computer 900 configured as illustrated in FIG. 12, for example.

FIG. 12 is a hardware configuration diagram illustrating an example of the computer 900 that implements functions of the device identification apparatus 1 according to the present embodiment. The computer 900 includes a central processing unit (CPU) 901, a read only memory (ROM) 902, a random access memory (RAM) 903, a hard disk drive (HDD) 904, an input-output interface (I/F) 905, a communication I/F 906, and a media I/F 907.

The CPU 901 operates in accordance with a program stored in the ROM 902 or the HDD 904, and performs control with the control unit 10 of FIG. 1. The ROM 902 stores a boot program that is executed by the CPU 901 when the computer 900 is activated, a program for the hardware of the computer 900 and the like.

The CPU 901 controls an input apparatus 910 such as a mouse and a keyboard, and an output apparatus 911 such as a display and a printer through the input-output I/F 905. Through the input-output I/F 905, the CPU 901 acquires data from the input apparatus 910, and outputs the generated data to the output apparatus 911.

The HDD 904 stores a program (device identification program) executed by the CPU 901, data used by the program, and the like. The communication I/F 906 receives data from another apparatus (not illustrated) (such as a network management apparatus) through a communication network (such as the network 5) and outputs it to the CPU 901, and transmits data generated by the CPU 901 to another apparatus through the communication network.

The media I/F 907 reads a program (device identification program) or data stored in a recording medium 912, and outputs it to the CPU 901 through the RAM 903. The CPU 901 loads, in the RAM 903, a program for an intended process from the recording medium 912 through the media I/F 907, and executes the loaded program. The recording medium 912 is an optical recording medium such as a digital versatile disc (DVD) and a phase change rewritable disk (PD), a magneto-optical recording medium such as a magneto optical disk (MO), a magnetic recording medium, a conductor memory tape medium, a semiconductor memory or the like.

For example, when the computer 900 functions as the device identification apparatus 1 according to the embodiment, the CPU 901 of the computer 900 executes a program loaded on the RAM 903 to implement the function of the device identification apparatus 1. In addition, the HDD 904 stores data in the RAM 903. The CPU 901 reads a program for an intended process from the recording medium 912 and executes it. Furthermore, the CPU 901 may read a program for an intended process from another apparatus through the communication network (the network 5).

EFFECTS OF THE INVENTION

Effects of the device identification apparatus are described below.

The device identification apparatus 1 according to the present invention includes: a communication information collection unit 101 configured to acquire communication information on existing devices indicating devices that exist and are connected to a network in models or types and acquire communication information on an identification target device indicating a device to be identified; a feature amount generation unit 102 configured to make the communication information of the existing devices feature amounts at a predetermined time interval, and generate feature amount data by assigning labels for identifying the models or types to the feature amounts to use the feature amount data as first training data, make the communication information of the identification target device feature amounts at a predetermined time interval, and generate feature amount data by assigning a dummy label to the feature amounts, to use the feature amount data as second training data, and further acquire communication information of the identification target device, make the communication information feature amounts at a predetermined time interval to generate feature amount data, and use the generated feature amount data as identification data; a machine learning unit 103 configured to cause a learning engine 3 to learn the first training data with the labels and the second training data with the dummy label, and input the identification data to the learning engine 3 that has learned the first training data and the second training data 1 to classify the feature amount data of the identification target device into the labels including the dummy label; a degree-of-similarity calculation unit 104 configured to calculate, based on the number of pieces of the feature amount data classified into the labels and the number of pieces of the feature amount data classified into the dummy label, a degree of similarity between a model or a type of the identification target device and each of the models or types indicated by the labels; and a device identification unit 105 configured to determine, for the degree of similarity of each of the labels, whether there is a label having a degree of similarity equal to or greater than a predetermined new type determination threshold, in accordance with a determination that there is a label having a degree of similarity equal to or greater than the predetermined new type determination threshold, identify the identification target device as an existing device of a model or type indicated by the label, and in accordance with a determination that there is no label having a degree of similarity equal to or greater than the predetermined new type determination threshold, identify the identification target device as a new type device different from the models or types indicated by the existing labels.

With this configuration, the device identification apparatus 1 can determine whether the device to be identified connected to the network is an existing model or type of device or a new type device by machine learning with high accuracy.

The device identification apparatus 1 further includes a new type determination threshold calculation unit 106 configured to calculate the predetermined new type determination threshold, wherein the new type determination threshold calculation unit 106 makes the communication information of the existing devices at a predetermined time interval feature amounts, assigns the labels to the feature amounts to generate feature amount data, divides each piece of the generated feature amount data with the labels into training data and test data, performs processing of selecting any one of the labels, further dividing the test data with the selected label into two, assigning a dummy label to one of the test data divided into two, causing the learning engine to learn the test data with the dummy label and the training data divided for each of the labels, and inputting the other of the test data divided into two to the learning engine that has learned the test data with the dummy label and the training data divided for each of the labels to classify the test data with the selected label into the labels including the dummy label, calculating a degree of similarity of the selected label to extract the degree of similarity as a degree of similarity of the device when there is training data, for each of the labels, performs processing of selecting any one of the labels, further dividing the test data of the selected label into two, assigning a dummy label to one of the test data divided into two, causing the learning engine to learn the test data with the dummy label and training data except training data of the selected label among the training data divided for the labels, inputting the other of the test data divided into two to the learning engine that has learned the test data with the dummy label and the training data except the training data of the selected label among the training data divided for the labels to classify the test data of the selected label into the labels including the dummy label and excluding the selected label, and calculating degrees of similarity for the labels to extract a label having the highest value among the calculated degrees of similarity as a degree of similarity of a device most similar when there is no training data, for each of the label, and calculates, for each of the labels, the new type determination threshold to be an intermediate value between a degree of similarity of a device when the training data exists and a degree of similarity of the most similar device when the training data does not exist.

In this way, the device identification apparatus 1 can set a more appropriate new type determination threshold based on the communication information of the existing devices on the network so as to be an intermediate value between the degree of similarity of the device when there is training data and the degree of similarity of the most similar device when there is no training data, for each label.

In the device identification apparatus 1, the device identification unit 105, upon identifying the identification target device as a new type device, outputs information on the device of new type to the new type determination threshold calculation unit 106, and the new type determination threshold calculation unit 106 adds the communication information of the device of new type to the communication information of the existing devices to perform the new type determination threshold calculating processing and updates the new type determination threshold.

In this way, when the identification target device is identified as a new type device, the device identification apparatus 1 can perform the new type determination threshold calculation processing by adding the device of new type to existing devices. Thus, the device identification apparatus 1 can automatically set an appropriate new type determination threshold.

REFERENCE SIGNS LIST

1 Device identification apparatus
3 Learning Engine
10 Control unit
11 Input/output unit
12 Storage unit
101 Communication information collection unit
102 Feature amount generation unit
103 Machine learning unit
104 Degree-of-similarity calculation unit
105 Device identification unit
106 New type determination threshold calculation unit
120 Accumulated data DB

The invention claimed is:

1. A device identification apparatus comprising:
a communication information collection unit, including one or more processors, configured to acquire communication information on existing devices indicating devices that exist and are connected to a network in models or types and acquire communication information on an identification target device indicating a device to be identified;
a feature amount generation unit, including one or more processors, configured to make the communication information of the existing devices feature amounts at a predetermined time interval, and generate feature amount data by assigning labels for identifying the models or the types to the feature amounts to use the feature amount data as first training data,
make the communication information of the identification target device feature amounts at a predetermined time interval, and generate feature amount data by assigning a dummy label to the feature amounts to use the feature amount data as second training data, and further acquire communication information of the identification target device, make the communication information feature amounts at a predetermined time interval to generate feature amount data, and use the generated feature amount data as identification data;
a machine learning unit, including one or more processors, configured to cause a learning engine to learn the first training data with the labels and the second training data with the dummy label, and input the identification data to the learning engine that has learned the first training data and the second training data to classify the feature amount data of the identification target device into the labels including the dummy label;

a degree-of-similarity calculation unit, including one or more processors, configured to calculate, based on the number of pieces of the feature amount data classified into the labels and the number of pieces of the feature amount data classified into the dummy label, a degree of similarity between a model or a type of the identification target device and each of the models or types indicated by the labels; and a device identification unit, including one or more processors, configured to determine, for the degree of similarity of each of the labels, whether there is a label having a degree of similarity equal to or greater than a predetermined new type determination threshold, in accordance with a determination that there is a label having a degree of similarity equal to or greater than the predetermined new type determination threshold, identify the identification target device as an existing device of a model or type indicated by the label, and in accordance with a determination that there is no label having a degree of similarity equal to or greater than the predetermined new type determination threshold, identify the identification target device as a new type device different from the models or types indicated by the existing labels.

2. The device identification apparatus according to claim 1, further comprising
a new type determination threshold calculation unit, including one or more processors, configured to calculate the predetermined new type determination threshold, wherein the new type determination threshold calculation unit is configured to:

make the communication information of the existing devices at a predetermined time interval feature amounts, assigns the labels to the feature amounts to generate feature amount data, divides each piece of the generated feature amount data with the labels into training data and test data, perform processing of selecting any one of the labels, further dividing the test data with the selected label into two, assigning a dummy label to one of the test data divided into two, causing the learning engine to learn the test data with the dummy label and the training data divided for each of the labels, inputting the other of the test data divided into two to the learning engine that has learned the test data with the dummy label and the training data divided for each of the labels to classify the test data with the selected label into the labels including the dummy label, calculating a degree of similarity of the selected label to extract the degree of similarity as a degree of similarity of the device when there is training data, for each of the labels, perform processing of selecting any one of the labels, further dividing the test data of the selected label into two, assigning a dummy label to one of the test data divided into two, causing the learning engine to learn the test data with the dummy label and training data except training data of the selected label among the training data divided for the labels, inputting the other of the test data divided into two to the learning engine that has learned the test data with the dummy label and the training data except the training data of the selected label among the training data divided for the labels to classify the test data of the selected label into the labels including the dummy label and excluding the selected label, and calculating degrees of similarity for the labels to extract a label having the highest value among the calculated degrees of similarity as a degree of similarity of a device most similar when there is no training data, for each of the label, and calculate, for each of the labels, the new type determination threshold to be an intermediate value between a degree of similarity of a device when the training data exists and a degree of similarity of the most similar device when the training data does not exist.

3. The device identification apparatus according to claim 2, wherein the device identification unit, upon identifying the identification target device as the device of new type, is configured to output information on the device of new type to the new type determination threshold calculation unit, and the new type determination threshold calculation unit is configured to add the communication information of the device of new type to the communication information of the existing devices to perform calculating processing of the new type determination threshold and updates the new type determination threshold.

4. A device identification method by a device identification apparatus that identifies a device connected to a network, the method including, at the device identification apparatus:

acquiring communication information on existing devices indicating existing devices connected to the network in models or types, and acquiring communication information on an identification target device indicating a device to be identified;

making the communication information of the existing devices feature amounts at a predetermined time interval, generating feature amount data by assigning labels for identifying the models or types to the feature amounts to use the feature amount data as first training data, making the communication information of the identification target device feature amounts at a predetermined time interval, generating feature amount data by assigning a dummy label to the feature amounts to use the feature amount data as second training data, and further acquiring communication information of the identification target device, and making the communication information feature amounts at a predetermined time interval to generate feature amount data, and using the generated feature amount data as identification data;

causing a learning engine to learn the first training data with the labels and the second training data with the dummy label, and inputting the identification data to the learning engine that has learned the first training data and the second training data to classify the feature amount data of the identification target device into the labels including the dummy label;

calculating, based on the number of pieces of the feature amount data classified into the labels and the number of pieces of the feature amount data classified into the dummy label, a degree of similarity between a model or type of the identification target device and a model or a type of indicated by each of the labels; and determining, for the degree of similarity of each of the labels, whether there is a label having a degree of similarity equal to or greater than a predetermined new type determination threshold, in accordance with a determination that there is a label having a degree of similarity equal to or greater than the predetermined new type determination threshold, identifying the identification target device as an existing device of a model or type indicated by the label, and in accordance with a determination that there is no label having a degree of similarity equal to or greater than the predetermined new type determination threshold, identifying the identification target device as a new type device different from the models or types indicated by the labels.

5. The device identification method according to claim 4, wherein the method further includes, at the device identification apparatus, making the communication information of the existing devices feature amounts at a predetermined time interval, assigning the labels to the feature amounts to generate feature amount data, dividing each piece of the generated feature amount data with the labels into training data and test data, performing processing of selecting any one of the labels, further dividing the test data with the selected label into two, assigning a dummy label to one of the test data divided into two, causing the learning engine to learn the test data with the dummy label and the training data divided for each of the labels, inputting the other of the test data divided into two to the learning engine that has learned the test data with the dummy label and the training data divided for each of the labels to classify the test data with the selected label into the labels including the dummy label, calculating a degree of similarity of the selected label to extract the degree of similarity as a degree of similarity of the device when there is training data, for each of the labels, performing processing of selecting any one of the labels, further dividing the test data of the selected label into two, assigning a dummy label to one of the test data divided into two, causing the learning engine to learn the test data with the dummy label and training data except training data of the selected label among the training data divided for the labels, inputting the other of the test data divided into two to the learning engine that has learned the test data with the dummy label and the training data except the training data of the selected label among the training data divided for the labels to classify test data of the selected label into the labels including the dummy label and excluding the selected label, and calculating degrees of similarity for the labels to extract a label having the highest value among the calculated degrees of similarity as a degree of similarity of a device most similar when there is no training data, for each of the label, and calculating, for each of the labels, the new type determination threshold to be an intermediate value between a degree of similarity of a device when the training data exists and a degree of similarity of the most similar device when the training data does not exist.

6. The device identification method according to claim 5, including, at the device identification apparatus, upon identifying the identification target device as the device of new type, adding the communication information of the device of new type to the communication information of the existing devices to perform calculating processing of the new type determination threshold and updating the new type determination threshold.

7. A non-transitory computer readable medium storing one or more instructions for causing a computer to execute:

acquiring communication information on existing devices indicating existing devices connected to a network in models or types, and acquiring communication information on an identification target device indicating a device to be identified;

making the communication information of the existing devices feature amounts at a predetermined time interval, generating feature amount data by assigning labels for identifying the models or types to the feature amounts to use the feature amount data as first training data, making the communication information of the identification target device feature amounts at a predetermined time interval, generating feature amount data by assigning a dummy label to the feature amounts to use the feature amount data as second training data, and further acquiring communication information of the identification target device, and making the communication information feature amounts at a predetermined time interval to generate feature amount data, and using the generated feature amount data as identification data;

causing a learning engine to learn the first training data with the labels and the second training data with the dummy label, and inputting the identification data to the learning engine that has learned the first training data and the second training data to classify the feature amount data of the identification target device into the labels including the dummy label;

calculating, based on the number of pieces of the feature amount data classified into the labels and the number of pieces of the feature amount data classified into the dummy label, a degree of similarity between a model or type of the identification target device and a model or a type of indicated by each of the labels; and determining, for the degree of similarity of each of the labels, whether there is a label having a degree of similarity equal to or greater than a predetermined new type determination threshold, in accordance with a determination that there is a label having a degree of similarity equal to or greater than the predetermined new type determination threshold, identifying the identification target device as an existing device of a model or type indicated by the label, and in accordance with a determination that there is no label having a degree of similarity equal to or greater than the predetermined new type determination threshold, identifying the identification target device as a new type device different from the models or types indicated by the labels.

8. The non-transitory computer readable medium according to claim 7, wherein the one or more instructions cause the computer to execute:

making the communication information of the existing devices feature amounts at a predetermined time interval, assigning the labels to the feature amounts to generate feature amount data, dividing each piece of the generated feature amount data with the labels into training data and test data, performing processing of selecting any one of the labels, further dividing the test data with the selected label into two, assigning a dummy label to one of the test data divided into two, causing the learning engine to learn the test data with the dummy label and the training data divided for each of the labels, inputting the other of the test data divided into two to the learning engine that has learned the test data with the dummy label and the training data divided for each of the labels to classify the test data with the selected label into the labels including the dummy label, calculating a degree of similarity of the selected label to extract the degree of similarity as a degree of similarity of a device when there is training data, for each of the labels, performing processing of selecting any one of the labels, further dividing the test data of the selected label into two, assigning a dummy label to one of the test data divided into two, causing the learning engine to learn the test data with the dummy label and training data except training data of the selected label among the training data divided for the labels, inputting the other of the test data divided into two to the learning engine that has learned the test data with the dummy label and the training data except the training data of the selected label among the training data divided for the labels to classify test data of the selected label into the labels including the dummy label and excluding the selected label, and calculating degrees of similarity for the labels to extract a label having the highest value among the calculated degrees of similarity as a degree of similarity of a device most similar when there is no training data, for each of the label, and calculating, for each of the labels, the new type determination threshold to be an intermediate value between a degree of similarity of a device when the training data exists and a degree of similarity of the most similar device when the training data does not exist.

9. The non-transitory computer readable medium according to claim 8, wherein the one or more instructions cause the computer to execute:

upon identifying the identification target device as the device of new type, adding the communication information of the device of new type to the communication information of the existing devices to perform calculating processing of the new type determination threshold and updating the new type determination threshold.

* * * * *